United States Patent
Uan et al.

(10) Patent No.: US 10,517,893 B2
(45) Date of Patent: Dec. 31, 2019

(54) CATIONIC BINDER, PHARMACEUTICAL COMPOSITION COMPRISING THE SAME AND METHOD OF USING THE SAME

(71) Applicants: CHANGHUA CHRISTIAN MEDICAL FOUNDATION CHANGHUA CHRISTIAN HOSPITAL, Changhua County (TW); National Chung Hsing University, Taichung (TW)

(72) Inventors: Jun-Yen Uan, Tainan (TW); Hung-Ming Wu, Taichung (TW)

(73) Assignees: CHANGHUA CHRISTIAN MEDICAL FOUNDATION CHANGHUA CHRISTIAN HOSPITAL, Changhua County (TW); National Chung Hsing University, Taichung (TW)

( * ) Notice: Subject to any disclaimer, the term of this patent is extended or adjusted under 35 U.S.C. 154(b) by 8 days.

(21) Appl. No.: 15/686,184

(22) Filed: Aug. 25, 2017

(65) Prior Publication Data
US 2019/0060360 A1    Feb. 28, 2019

(51) Int. Cl.
*A61K 33/26*    (2006.01)
*A61K 33/08*    (2006.01)

(52) U.S. Cl.
CPC .............. *A61K 33/26* (2013.01); *A61K 33/08* (2013.01)

(58) Field of Classification Search
None
See application file for complete search history.

(56) References Cited

U.S. PATENT DOCUMENTS 5,976,401 A * 11/1999 Suzuki .................... C02F 1/281
                                                    210/683

OTHER PUBLICATIONS

Malberti, Fabio, Hyperphosphatemia: Treatment options, Drugs (2013) 73:673-688. (Year: 2013).*
Lung, Synthesis of Mg—Fe—Cl hydrotalcite-like nanoplatelets as an oral phosphate binder: evaluations of phosphorus intercalation activity and cellular cytotoxicity, Sci Rep. Sep. 1, 2016;6:32458. doi: 10.1038/srep32458.

* cited by examiner

Primary Examiner — Robert A Wax
Assistant Examiner — Melissa S Mercier
(74) Attorney, Agent, or Firm — Winston Hsu (57) ABSTRACT

The present invention provides a pharmaceutical composition for treating a patient suffering from or predisposed to hyperphosphatemia, which contains Mg—Fe—Cl HCln. In one embodiment, the Mg—Fe—Cl HCln is shown in formula (I). The phosphorus uptaking capacity of the pharmaceutical composition is greater than 100 ppm/(g/L). The present invention further provides a method for treating a patient suffering from or predisposed to hyperphosphatemia by using said pharmaceutical composition. The present invention further provides a method of manufacturing the pharmaceutical composition.

20 Claims, 11 Drawing Sheets

CATIONIC BINDER, PHARMACEUTICAL COMPOSITION COMPRISING THE SAME AND METHOD OF USING THE SAME

BACKGROUND OF THE INVENTION

1. Field of the Invention

The present invention is related to a cationic binder, and a pharmaceutical composition for treating a patient suffering from or predisposed to hyperphosphatemia and a method of using the same, and more particularly, to a cationic binder including magnesium, iron and chloride and a pharmaceutical composition including the same, and a method of using the same.

2. Description of the Prior Art

It is well known that patients suffering from chronic kidney deficiency in most instances also suffer from a disorder in calcium- and phosphorous-self-regulation. Therefore as most frequently, concomitant disease in renal deficiencies renal osteopathy must be mentioned.

In renal osteopathy a decrease in intestinal calcium resorption followed by a decrease in calcium intercalation into bones leads to so called hypocalcaemia (acalcinosis) which finds its expression in mineralisation deficiencies and osteoporosis. Additionally in renal osteopathy insufficient phosphorous excretion can be noticed resulting in an increase of phosphorous levels in blood leading to hyperphosphataemia. The interaction of both phenomena manifests in secondary hyperparathyroidism leading to skeleton destruction.

Therefore in renal deficiencies such as especially chronic kidney diseases a careful control of phosphorous accumulation in the intestine and in blood or serum is necessary in order to prevent secondary hyperparathyroidism and metastatic calicification.

SUMMARY OF THE INVENTION

The present invention therefore provides a cationic binder that can bind an anion such as phosphate. The cationic binder can be used as a pharmaceutical composition for treating a patient suffering from hyperphosphatemia, or uses as a pharmaceutical composition for prophylactically treating a patient predisposed to hyperphosphatemia.

According to one embodiment, a cationic binder is provided. It includes magnesium, iron (III) and chloride, and an atomic ratio of $Mg^{+2}$ and $Fe^{+3}$ from raw materials used for synthesizing the cationic binder is between 2:1 and 60:1, and an anion uptaking capacity of the cationic binder is greater than 100 ppm/(g/L).

According to one embodiment, a pharmaceutical composition for treating a patient suffering from or predisposed to hyperphosphatemia is provided. The pharmaceutical composition includes a cationic binder and a pharmaceutically acceptable carrier, wherein the cationic binder comprises magnesium, iron (III) and chloride, and an atomic ratio of $Mg^{+2}$ and $Fe^{+3}$ from raw materials used for synthesizing the cationic binder is between 2:1 and 60:1, and a anion uptaking capacity of the cationic binder is greater than 100 ppm/(g/L).

According to another embodiment, a method for treating or prophylactically treating a patient suffering from or predisposed to hyperphosphatemia is provided. The method includes administering a pharmaceutical composition to the patient, wherein the cationic binder comprises magnesium, iron (III) and chloride, and an atomic ratio of $Mg^{+2}$ and $Fe^{+3}$ from raw materials used for synthesizing the cationic binder is between 2:1 and 60:1, and an anion uptaking capacity of the cationic binder is greater than 100 ppm/(g/L).

These and other objectives of the present invention will no doubt become obvious to those of ordinary skill in the art after reading the following detailed description of the preferred embodiment that is illustrated in the various figures and drawings.

DETAILED DESCRIPTION

To provide a better understanding of the present invention, preferred embodiments will be described in detail. The preferred embodiments of the present invention are illustrated in the accompanying drawings with numbered elements.

The patients with end-stage of renal disease (ESRD) need to take oral phosphate binder. Traditional phosphate binders may leave the disadvantage of aluminum intoxication or cardiac calcification. Herein, Mg—Fe—Cl hydrotalcite-like nanoplatelet (HTln) is for the first time characterized as potential oral phosphate binder, with respect to its phosphorus uptake capacity in cow milk and cellular cytotoxicity. A novel method was developed for synthesizing the Mg—Fe—Cl HTln powder in different $Mg^{2+}:Fe^{3+}$ ratios from the raw materials, $Mg(OH)_2$ and $FeCl_3.6H_2O$, wherein an atomic ratio of $Mg^{+2}$ and $Fe^{+3}$ from $Mg(OH)_2$ and $FeCl_3.6H_2O$ is between 2:1 and 60:1. A ratio of $Mg^{2+}:Fe^{3+}$ in the cationic binder is between 6.0:1 and 1.5:1, preferably 4.0:1 and 2.0:1, and the optimization is 2.8:1. In one embodiment, the Mg—Fe—Cl HTln is shown in formula (I):

formula (I)

It is demonstrated that addition of 0.5 g Mg—Fe—Cl HTln in cow milk could reduce its phosphorus content by 40% in 30 min, exhibiting a phosphate uptaking capacity of 150 ppm/(g/L), and reduced by 65% in 90 min, exhibiting a phosphate uptaking capacity of 325 ppm/(g/L). In low pH environment, the Mg—Fe—Cl HTln could exhibit relatively high performance for uptaking phosphorus. During a 90 min reaction of the HTln in milk, no phosphorus restoration occurred. In-vitro cytotoxicity assay of Mg—Fe—Cl HTln revealed no potential cellular cytotoxicity. The cells that were cultured in the HTln extract-containing media are even more viable than cells that were cultured in extract-free media (blank control). The Mg—Fe—Cl HTln extract led to hundred ppm of Mg ion and some ppm of Fe ion in the media, should be a positive effect on the good cell viability. Further, a dosage between 10 mg/kg and 30 mg/kg by dietary treatment can reduce the serum levels of blood urea nitrogen (BUM), creatinine and phosphorus, showing its superior effect on treating renal disease.

The following context will show the experiment regarding to the phosphate uptaking capacity and effect on treating renal disease of the cationic binder (Mg—Fe—Cl HTln) provided by the present invention.

EXPERIMENT 1

Synthesis and Characterization and Characterization of Synthesized Mg—Fe—Cl HTln $Mg(OH)_2$ and $FeCl_3.6H_2O$ powders were utilized to synthesize Mg—Fe—Cl HTln. In Table 1, A represents $Mg(OH)_2$ and B represents $FeCl_3.6H_2O$. Three powder samples, each containing A and B, denoted as 2A_0.1B, 2A_0.4B and 2A_0.6B. Each powder sample was immersed in 500 ml distilled water at 50° C. The pH of the aqueous solution was adjusted to, and maintained at, pH 1 by adding HCl (aq) to totally dissolve the chemicals. The pH of the ionic solution was then increased up to 9.5 by adding NaOH(aq)(2.5 M) dropwise. When the pH value was stable at pH 9.5 at 50° C., a reddish-brown suspension was present in the solution. The solution pH was maintained at pH 9.5 for 2 hr at 50° C. The above mixture was vigorously stirred magnetically and bubbled by forcing 1 LPM Ar gas into the aqueous solution throughout the synthesis. The solution with the reddish-brown suspension was then extracted using a centrifuge, rinsed five times with distilled water, and then vacuum dried. The crystallographic structures of synthetic products were identified by X-ray powder diffraction using a Bruker D2 Phaser diffractometer. Ni filtered Cu Kα 1 (1.5406 Å) radiation was used for this purpose. The synthetic products also underwent Fourier transform infrared (FT-IR) analysis on a Perkin-Elmer Spectrum RX-I spectrometer. For the FT-IR analysis, 0.002 g HTln powder, mixed with 0.2 g oven-dried (80° C., 1 h) spectroscopic-grade KBr, was pressed into a disc of diameter 12.91 mm under 8 tons of pressure for one minute in a vacuum. FT-IR spectra at wavenumbers of 400 to 4000 $cm^{-1}$ were obtained. Elemental chemical analyses of synthetic products were performed by X-ray Photoelectron Spectroscopy (XPS). A JEOL JSM-7000F field emission scanning electron microscope was used to observe the topography of the synthetic products.

TABLE 1

| A<br>$Mg(OH)_2$ | B<br>$FeCl_3·6H_2O$ | Designation of the compound produced hereafter |
|---|---|---|
| 2 g | 0.1 g | 2A_0.1B |
| 2 g | 0.4 g | 2A_0.4B |
| 2 g | 0.6 g | 2A_0.6B |

Figure 1:
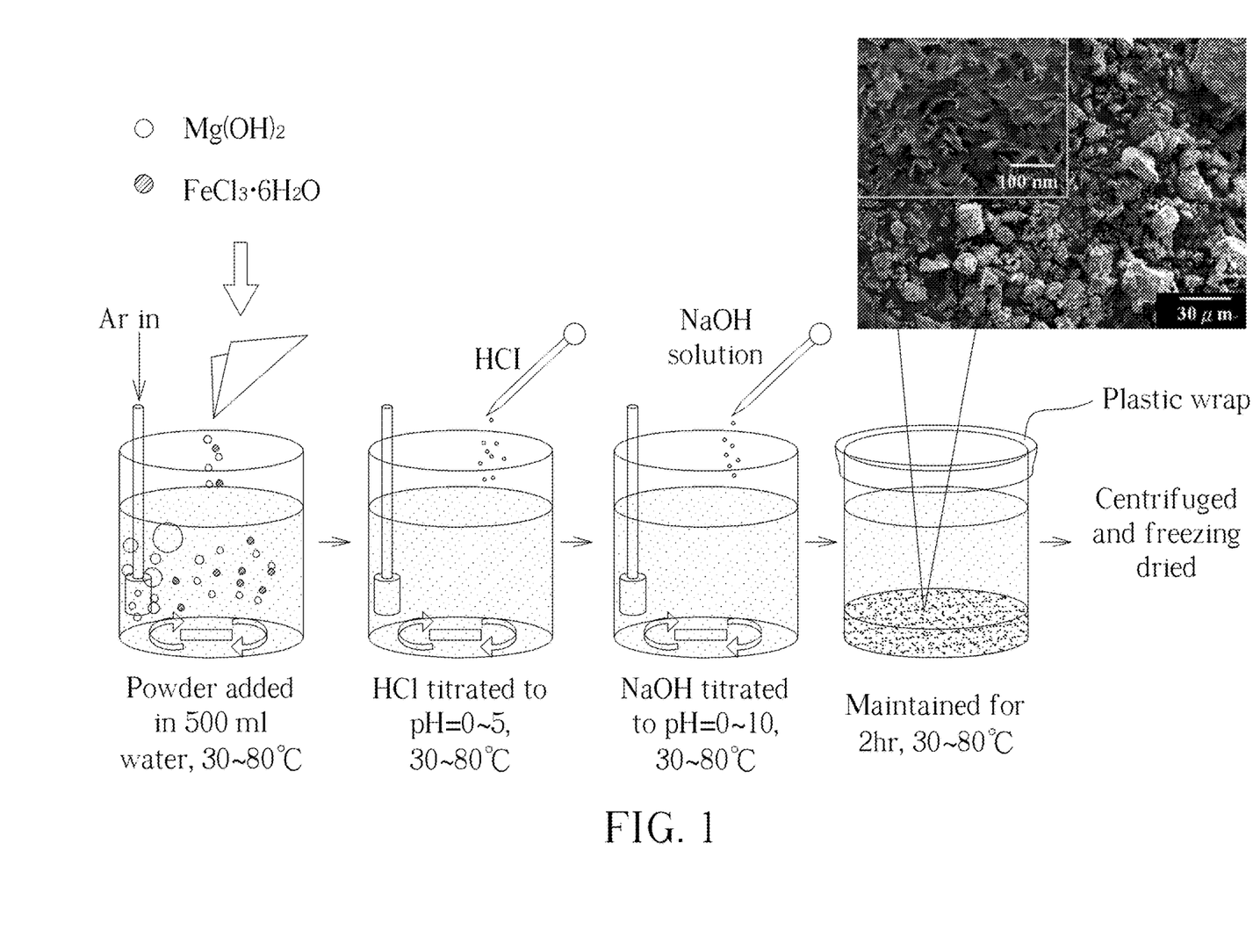
FIG. 1 shows a schematic diagram of formation of Mg—Fe—Cl hydrotalcite-like nanoplatelet (HTln).
Figure 2A:
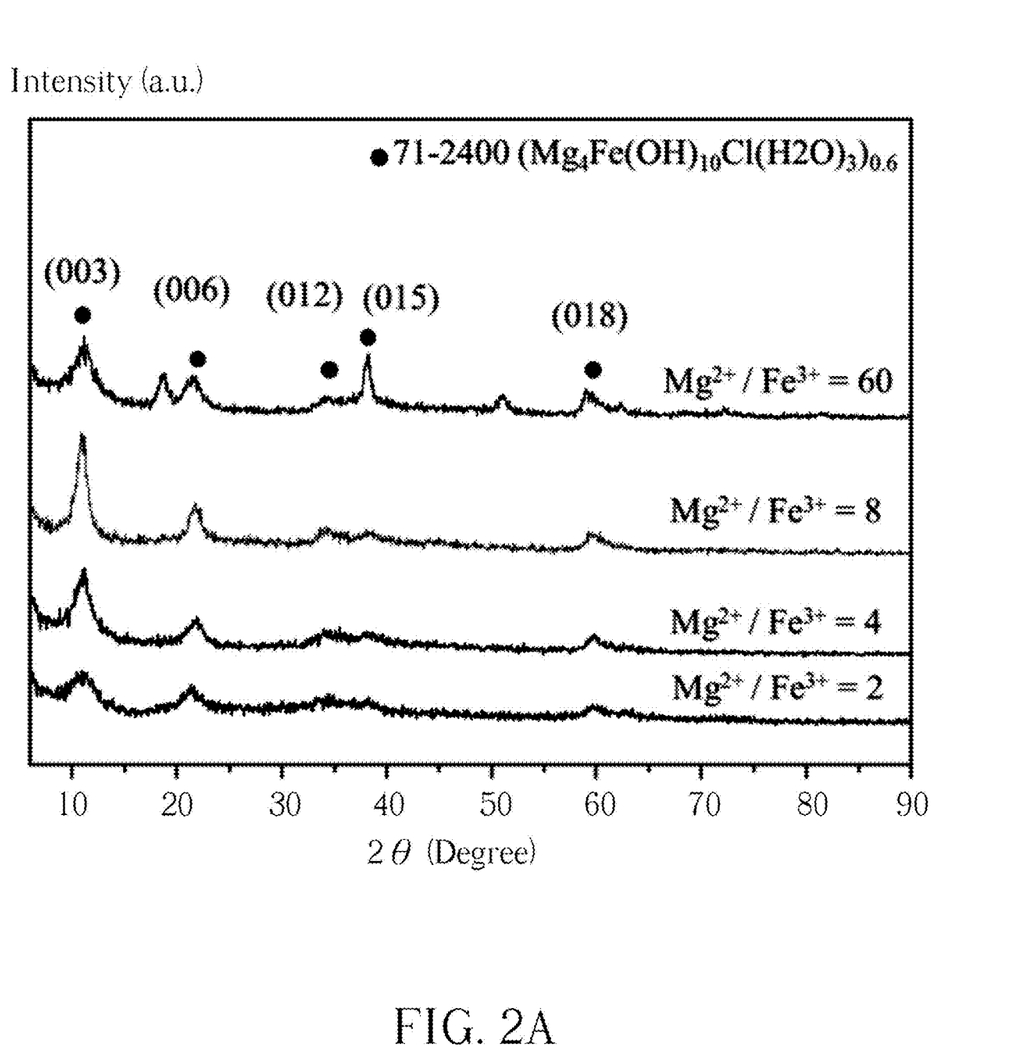
FIG. 2A shows the X-ray diffraction patterns of the Mg—Fe—Cl Htln powders with the different $Mg^{+2}/Fe^{+3}$ molar ratios for synthesizing the compounds.
Figure 2B:
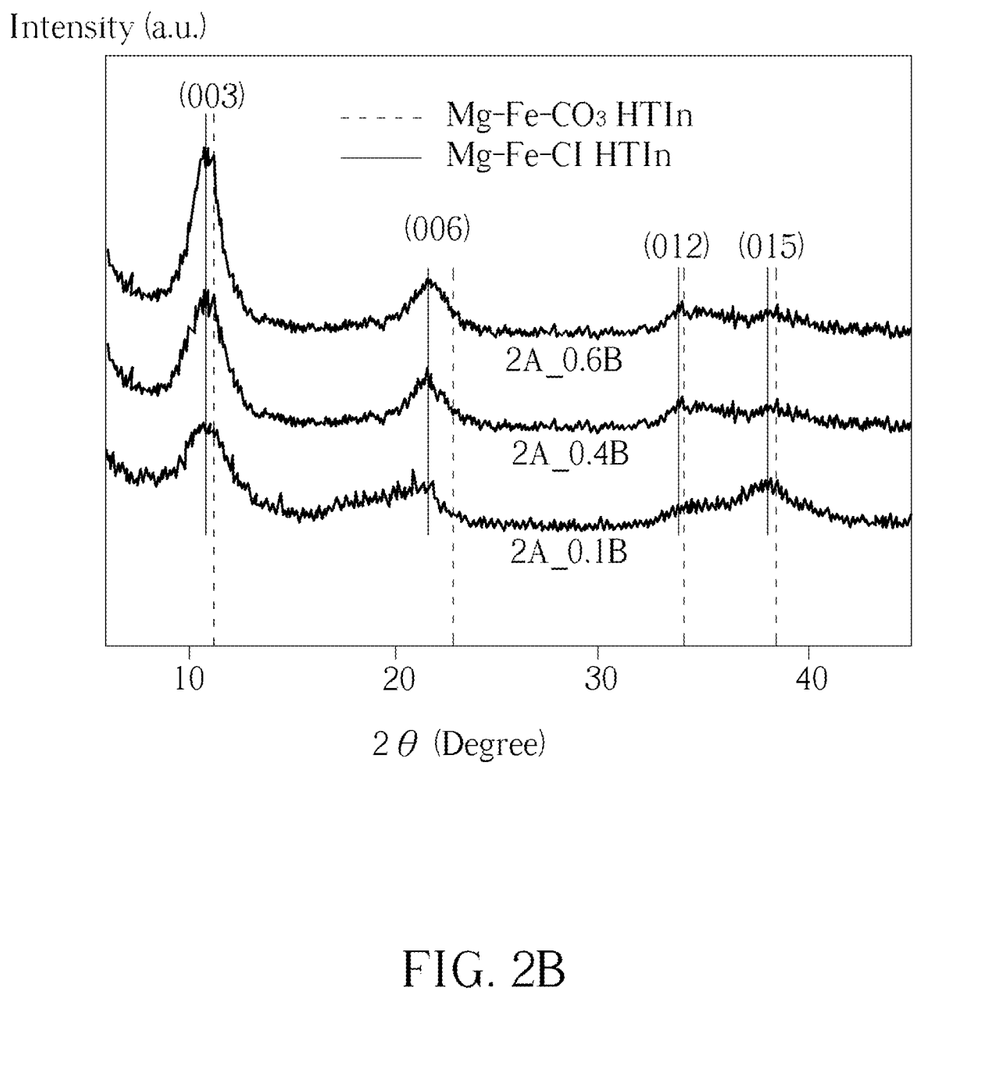
FIG. 2B presents the X-ray powder diffraction patterns of the synthesized Mg—Fe—Cl HTln powder.

Please refer to FIG. 1, FIG. 2A and FIG. 2B, wherein FIG. 1 shows a schematic diagram of formation of Mg—Fe—Cl hydrotalcite-like nanoplatelet (HTln), FIG. 2A shows the X-ray diffraction patterns of the Mg—Fe—Cl Htln powders with the different $Mg^{+2}/Fe^{+3}$ molar ratios for synthesizing the compounds and FIG. 2B shows the X-ray powder diffraction patterns of the synthesized Mg—Fe—Cl HTln powder. In FIG. 1, the inset in the SEM image shows the nanoplatelet structure of HTln. The preparation conditions for the synthesis of Mg—Fe—Cl HTln have been illustrated in Table 1, FIG. 2A shows the X-ray diffraction patterns of the Mg—Fe—Cl Htln powders with the different $Mg^{+2}/Fe^{+3}$ molar ratios for synthesizing the compounds. $Mg(OH)_2$ and $FeCl_3.6H_2O$ are the raw materials for the synthetization. In FIG. 2B, $Mg^{+2}/Fe^{+3}$ molar ratios represent the atomic ratio of $Mg^{+2}$ and $Fe^{+3}$ from the raw material used for the synthetization. The X-ray diffraction patterns of the $Mg^{+2}/Fe^{+3}$ molar ratios 2, 4, 8 and 60 were plotted from bottom to up in FIG. 2B. The characteristic peaks at around 2θ=11° and 22° corresponded to typical basal spacing ($d_{003}$) and ($d_{006}$) of LDH phases, respectively. As shown in FIG. 2B, the reflection peaks at 10.90° and 21.65° were identified as basal reflections (003) and (006) from hydrotalcite. The (003) basal spacing, 8.11 Å, of the Mg—Fe—Cl HTln is similar to that of the Mg—Fe—Cl HTln obtained by conventional methods. The (003) basal spacing (8.11 Å) of the HTln herein exceeds that of Mg—Fe—$CO_3$HTln (7.97 Å). As presented in FIG. 2B, each of the X-ray intensity peaks of the Mg—Fe—Cl HTln were shifted toward lower angles from corresponding X-ray peaks of Mg—Fe—$CO_3$ HTln, revealing that the carbonate ion was not the main intercalation anion. Although preventing contamination from carbonate ions in the preparation of HTln is difficult, the synthetic method that was developed herein successfully minimizes carbonate contamination. Based on the X-ray reflection patterns in FIG. 2B, the HTln that was made from 2A_0.6B exhibited much greater crystallinity than those made from 2A_0.1B and 2A_0.4B. Table 2 presents the $Mg^{2+}$, $Fe^{3+}$, $Cl^-$ and $Na^+$ contents (in at. %), obtained by XPS, of the samples 2A_0.1B, 2A_0.4B and 2A_0.6B. The chemical contents of each sample were calculated from its corresponding Mg 2p, Fe 2p3, Cl 2p and Na 1 s XPS spectra. In Table 2, A_0.1B contained 0.8% $Cl^-$; 2A_0.4B contained 1.2% $Cl^-$, and 2A_0.6B contained 2.3% of $Cl^-$. Importantly, sodium was not detected in the various samples, supporting the finding that $Cl^-$ was not associated with the residual NaCl but was intercalated in the HTln. The general formula for HTln is of the form $[M_{1-x}^{2+}M_x^{3+}(OH)_2]^{x+}(A_{x/n}^{n-}) \cdot nH_2O^1$, where x equals to $M^{2+}/(M^{2+}+M^{3+})$. Table 2 presents the x values of 2A_0.1B, 2A_0.4B and 2 A_0.6B. The x value of 2A_0.6B is 0.26. In the present invention, the ratio for 2A_0.6B is 2.8:1 which is close to the optimal ratio. Therefore, based on the synthesis method explored herein, 2A_0.6B was used to synthesize Mg—Fe—Cl HTln for the following phosphate binding experiments.

EXPERIMENT 2

Anionic Sorption and Desorption of Mg—Fe—Cl HTln in Aqueous $KH_2PO_4$

Aqueous $KH_2PO_4$(100 ml), comprising about 1000 ppm $PO_4^{3-}$, was used to evaluate the ability of the synthesized Mg—Fe—Cl HTln powder to take up $PO_4^{3-}$ from the $KH_2PO_4$ aqueous. In each experimental run, 0.2 g of the Mg—Fe—Cl HTln powder was immersed in 100 ml aqueous $KH^2PO^4$. Each solution in the experiment was purged with argon to reduce the formation of carbonate anions from the atmospheric gaseous $CO_2$. The concentrations of $Cl^-$ and residual $PO_4^{3-}$ in the aqueous $KH_2PO_4$ were simultaneously measured using ion chromatography (IC; ICS-900, DIONEX). Dilute nitric acid (2 vol. %) was used to maintain the pH of the aqueous at pH 3.0±0.2 or pH 6.0±0.2 throughout the anion sorption and desorption experiment. The error in the $PO_4^{3-}$ concentration that arose from the addition of aqueous nitric acid to maintain the solution pH was less than 5%.

Figure 3:
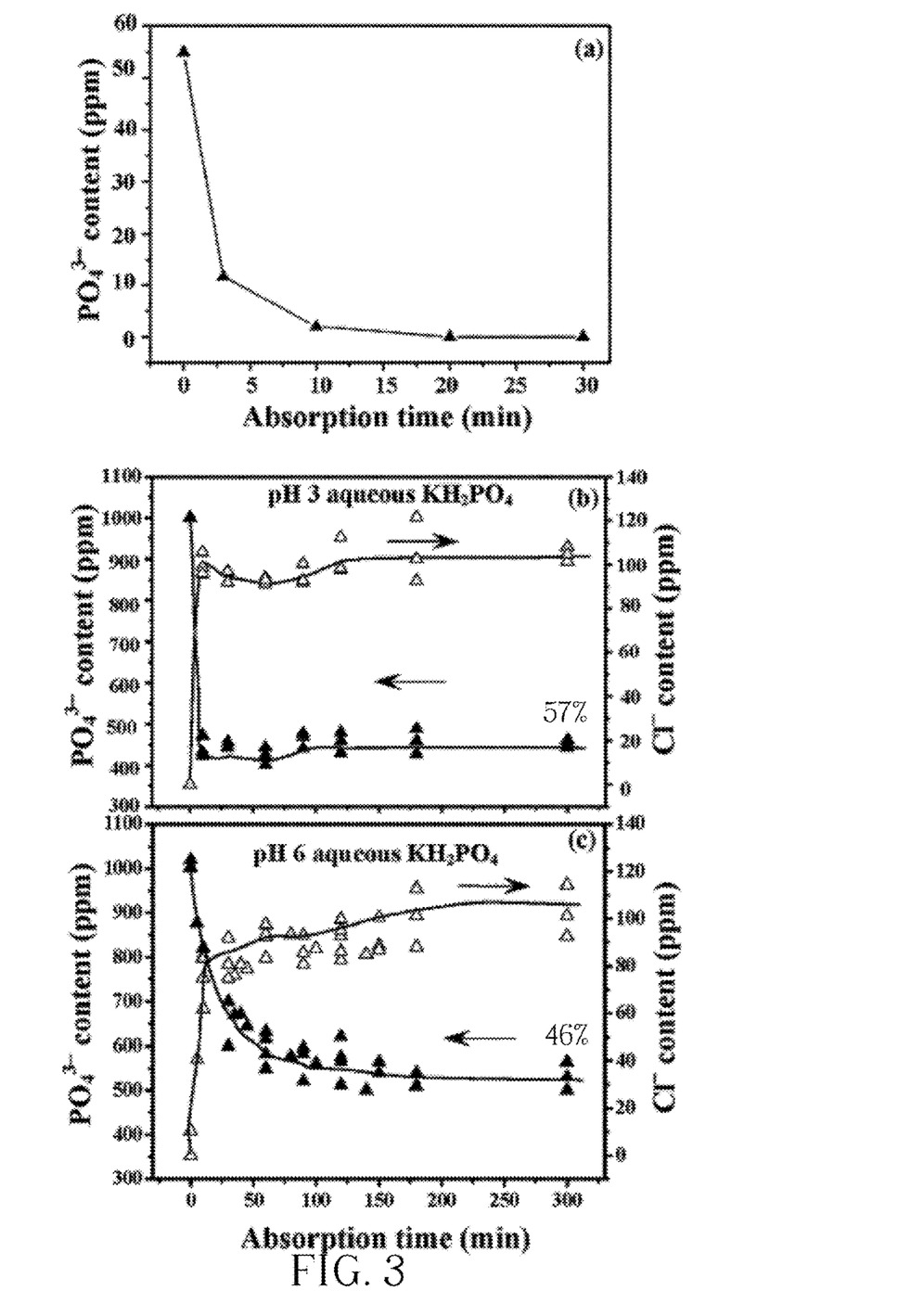
FIG. 3 shows the $PO_4^{3-}$ sorption after addition of HTln powder.

Please refer to FIG. 3, which shows the $PO_4^{3-}$ sorption after addition of HTln powder wherein (a) shows $PO_4^{3-}$ sorption by 0.2 g Mg—Fe—Cl HTln in 100 ml aqueous $KH_2PO_4$ (original 55 ppm of $PO_4^{3-}$); (b, c) shows $PO_4^{3-}$ sorption and $Cl^-$ desorption when immersing 0.2 g Mg—Fe—Cl HTln in 100 ml aqueous $KH_2PO_4$ (original 1000 ppm of $PO_4^{3-}$), where (b) sorption and desorption experiments being conducted at pH 3, (c) sorption and desorption experiments being conducted at pH 6. The phosphate uptaking capacity of Me—Fe—Cl HTCln is calculated by equation (I).

$$\text{Phosphorus uptaking capacity (ppm/(g/L))} = \frac{\left[\frac{\text{phosphate weight in original solution (mg)} \times \text{sorption rate \%}}{\text{solution volume used in the test (L)}}\right] (\text{ppm})}{\left[\frac{HTln \text{ powder weight}}{\text{solution volume used in the test}}\right] (\text{g/L})} \quad (\text{ppm/(g/L)}) \quad \text{Equation (I)}$$

As shown in FIG. 3(a), when 0.2 g HTln powder is added to 100 ml aqueous $KH_2PO_4$(which initially contained 55 ppm of $PO_4^{3-}$) at room temperature, the HTln took up almost all $PO_4^{3-}$ in the solution in 20 min. To determine the $PO_4^{3-}$-uptaking capacity of the Mg—Fe—Cl HTln, 0.2 g of the HTln powder was added to 100 ml aqueous $KH_2PO_4$ with a $PO_4^{3-}$ initial content of 1000 ppm (FIG. 3). FIG. 3(b) reveals that when 0.2 g of Mg—Fe—Cl HTln was added to the 100 ml aqueous $KH_2PO_4$ maintained at pH 3, with an original $PO_4^{3-}$ concentration 1000 ppm, the solution only ~430 ppm of residual $PO_4^{3-}$ (57% phosphate uptake) after 10 min, and almost no more $PO_4^{3-}$ was taken up from 10 min to 300 min.

During the same experimental period, the chloride anion was de-intercalated from the Mg—Fe—Cl HTln, providing evidence of anion intercalation and de-intercalation. FIG. 3(c) shows that 0.2 g Mg—Fe—Cl HTln in 100 ml aqueous $KH_2PO_4$ with 1000 ppm of $PO_4^{3-}$ at pH 6 took up $PO_4^{3-}$, reducing the phosphate content to ~540 ppm in 100 min, and almost no more $PO_4^{3-}$ was taken up from 100 min to 300 min. The phosphate uptake capacity of the Mg—Fe—Cl HTln herein in aqueous $KH_2PO_4$ at pH 6 was ~46%, lower than that of the HTln at pH 3.

As shown in FIG. 3(b), Mg—Fe—Cl HTln powder in aqueous $KH_2PO_4$ at pH 3 exhibited an excellent ability to take up phosphate from acidic solution, reducing the phosphate concentration from ~1000 ppm down to ~450 ppm. Importantly, during the 5 hr uptake of phosphate in aqueous $KH_2PO_4$ with pH fixed at pH 3, the HTln was stably maintained the phosphate content of the aqueous $KH_2PO_4$ at ~450 ppm throughout the experimental period, suggesting that the HTln structure did not disintegrate under acidic conditions, so phosphate restoration did not occur. The concentration of chloride increased during this period, indicating direct evidence of anion exchange. Table 3 summarizes the phosphorus uptaking capability of Mg—Fe—Cl HTln at pH 3 and pH 1. The phosphorus uptaking capability of Mg—Fe—Cl HTln in the present invention is at least 100 ppm/(g/L), or even greater than 200 ppm/(g/L).

TABLE 3

| | pH 3 | | pH 1 | |
|---|---|---|---|---|
| | Sorption rate % | $PO_4^{-3}$ uptaking capability ppm/(g/L) | Sorption rate % | $PO_4^{-3}$ uptaking capability ppm/(g/L) |
| 8:1 | 53.6 | 268 | 53.2 | 266 |
| 4:1 | 54.4 | 272 | 55.7 | 278.5 |
| 2:1 | 48 | 240 | 54.9 | 274.5 |

EXPERIMENT 3

Mg—Fe—Cl HTln Powder and Sevelamer Hydrochloride (Renagel) in Cow Milk and Characterization Thereof Following Phosphorus Uptake Experiments The phosphate binding performance of Mg—Fe—Cl HTln powder was compared with that of a commercial phosphate binder, sevelamer hydrochloride (Renagel) in cow milk. To 25 ml cow milk were added 0.5 g Mg—Fe—Cl HTln or 1 g Mg—Fe—Cl HTln or 1 g of sevelamer hydrochloride powder. The original pH of the milk was around 6.7. Two experimental approaches were used to study the effect of pH on the ability of the HTln to take up phosphorus. In the first, the pH of the milk was adjusted to pH 6.0±0.2 by adding aqueous $HNO_3$ (50 vol. %), and this pH value was consistently maintained throughout the phosphorus uptake experiment. In the second, the milk pH was not maintained at a constant value during the phosphorus uptake experiment. Concentrations of residual phosphorus (mg/kg, ppm by mass) in the milk were measured by inductively coupled plasma atomic emission spectroscopy (ICP-AES) using US EPA method 3050B. The above quantitative analyses were carried out by Chemical Laboratory-Taipei, SGS TAIWAN LTD. X-ray powder diffraction was used to compare the Mg—Fe—Cl HTln before phosphorus uptake with that after phosphorus uptake. Fourier transform infrared (FT-IR) analyses were performed to obtain the spectra of both Mg—Fe—Cl HTln and sevelamer hydrochloride (Renagel) before and after the uptake of phosphorus in cow milk. To measure the volume changes of Mg—Fe—Cl HTln and sevelamer hydrochloride (Renagel) after each of the binders was mixed with cow milk for 90 min, a 25 ml capacity graduated cylinder with graduation marks every 0.5 ml was used. A 0.5 g mass of Mg—Fe—Cl HTln or 0.5 g sevelamer hydrochloride (Renagel) was mixed with 7 ml milk in the cylinder. The initial volume was read right immediately after mixing. The volume was read again after 90 min. The volume change ($\Delta V$ %) was thus obtained.

Figure 4:
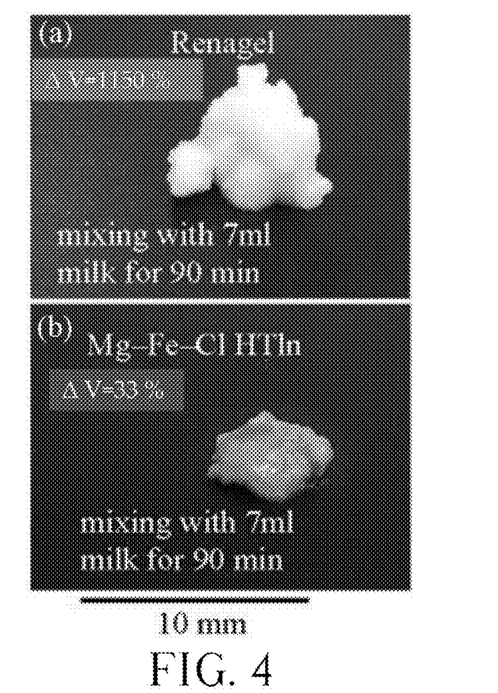
FIG. 4 shows images of Renagel (FIG. 4(a)) and Mg—Fe—Cl HTln (FIG. 4(b)) before and after mixing with 7 ml of milk for 90 min.
Figure 5:
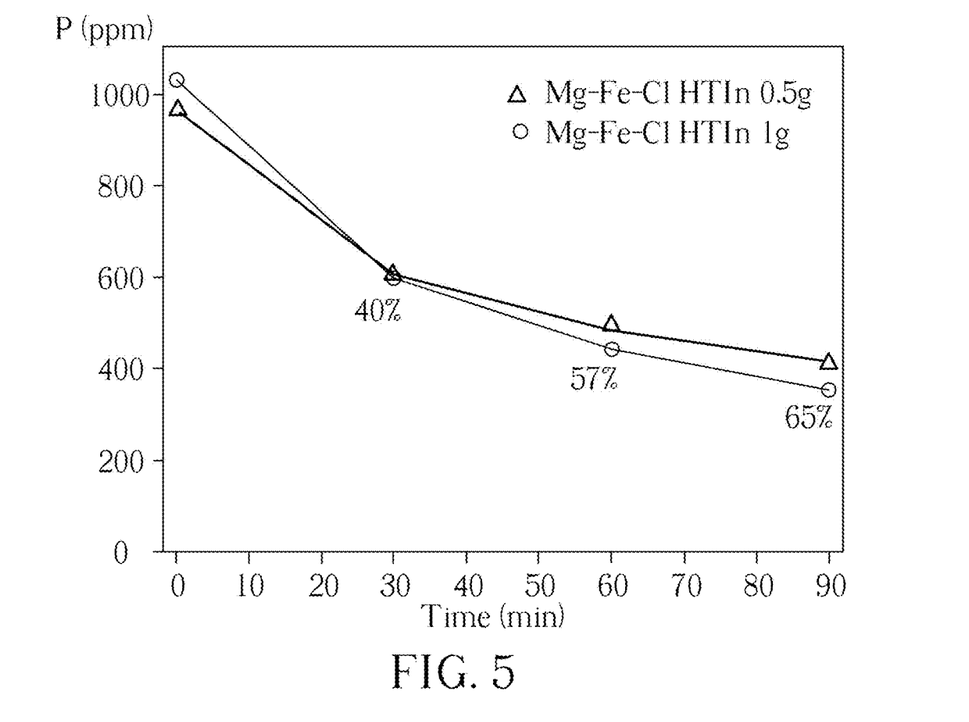
FIG. 5 presents the dietary phosphorus-binding performance of Mg—Fe—Cl HTln in milk at pH 6.

Please refer to FIG. 4, which shows images of Renagel (FIG. 4(*a*)) and Mg—Fe—Cl HTln (FIG. 4(*b*)) after mixing with 7 ml of milk for 90 min. In at least three in vitro swelling tests, 0.5 g Renagel powder has been shown to swell by approximately 1150% in volume when placed in milk. In an identical test, 0.5 g of Mg—Fe—Cl HTln powder was found to swell by only ~33 vol. % when placed in milk. As shown, the slurry of 0.5 g Renagel had a greater volume than that of 0.5 g Mg—Fe—Cl HTln. FIG. 5 presents the dietary phosphorus-binding performance of Mg—Fe—Cl HTln in milk at pH 6, which falls in the gastric pH range of 5 to 6.7 (which is the highest recorded pH within 5 min of eating) during a meal. In digestion, the stomach forms chime, which is transferred to the duodenum. The small intestine is critical in phosphate absorption. Therefore, removing most of the phosphate using a phosphate binder during digestion in the stomach is important for ESRD patients. The following experiments were performed for 90 min since most of a meal was digested in the stomach, which was usually emptied of food in approximately 90 min. A 0.5 g mass of Mg—Fe—Cl HTln (added to 25 ml milk at pH 6) efficiently reduced the phosphorus content by approximately 40% in 30 min, and reduced it by ~65% after 90 min, as presented in FIG. 5. Moreover, phosphorus binding by 1 g Mg—Fe—Cl HTln (in 25 ml milk at pH 6) is similar in extent to that by the 0.5 g Mg—Fe—Cl HTln. In comparison, the phosphorus binding performance of Renagel in pH 7 environments is much lower than that of the Renagel in pH 3. Mg—Fe—Cl HTln has similar result, as shown in FIG. 3(*b*,*c*), that the HTln in pH 6 solution exhibited a relatively low phosphorous binding performance. Therefore, as the data plots in FIG. 5, samples 0.5 g and 1 g exhibited similar performance to take up phosphorus, which may be due to the negative effect of pH 6 in tested milk.

Figure 6:
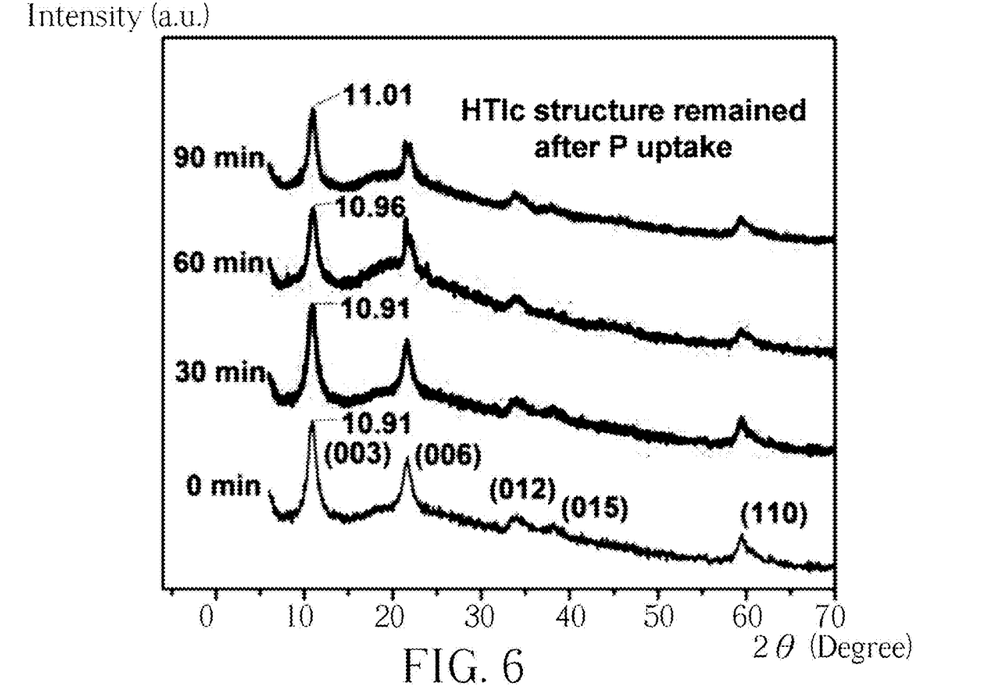
FIG. 6 presents the X-ray diffraction patterns of the Mg—Fe—Cl HTln before and after the phosphorus binding experiments in milk for 90 min.
Figure 7A:
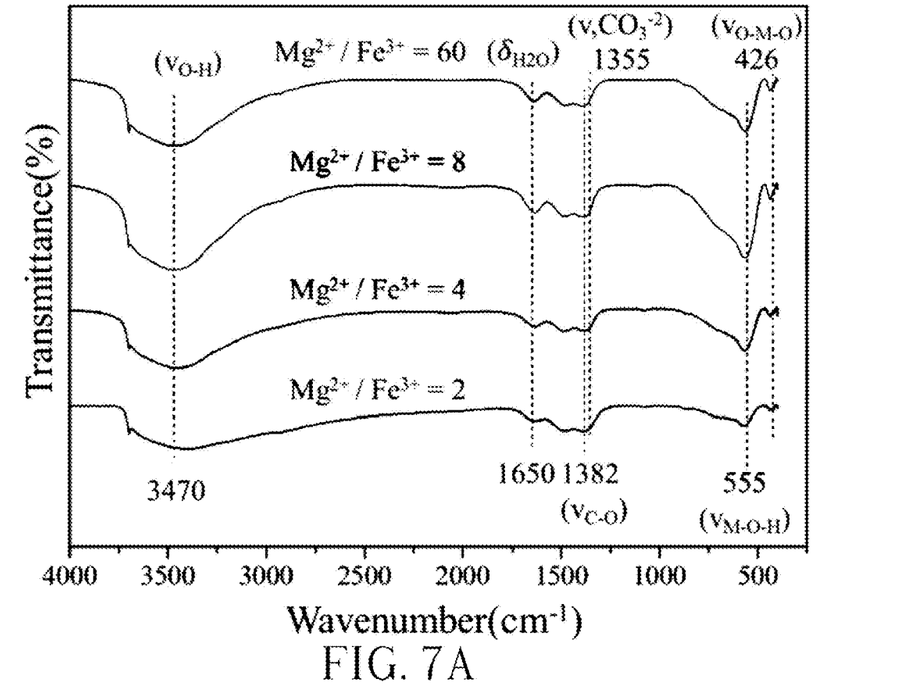
FIG. 7A shows the FT-IR spectra of the Mg—Fe—Cl Htln powders with different $Mg^{+2}/Fe^{+3}$ molar ratios for synthesizing the compounds.
Figure 7B:
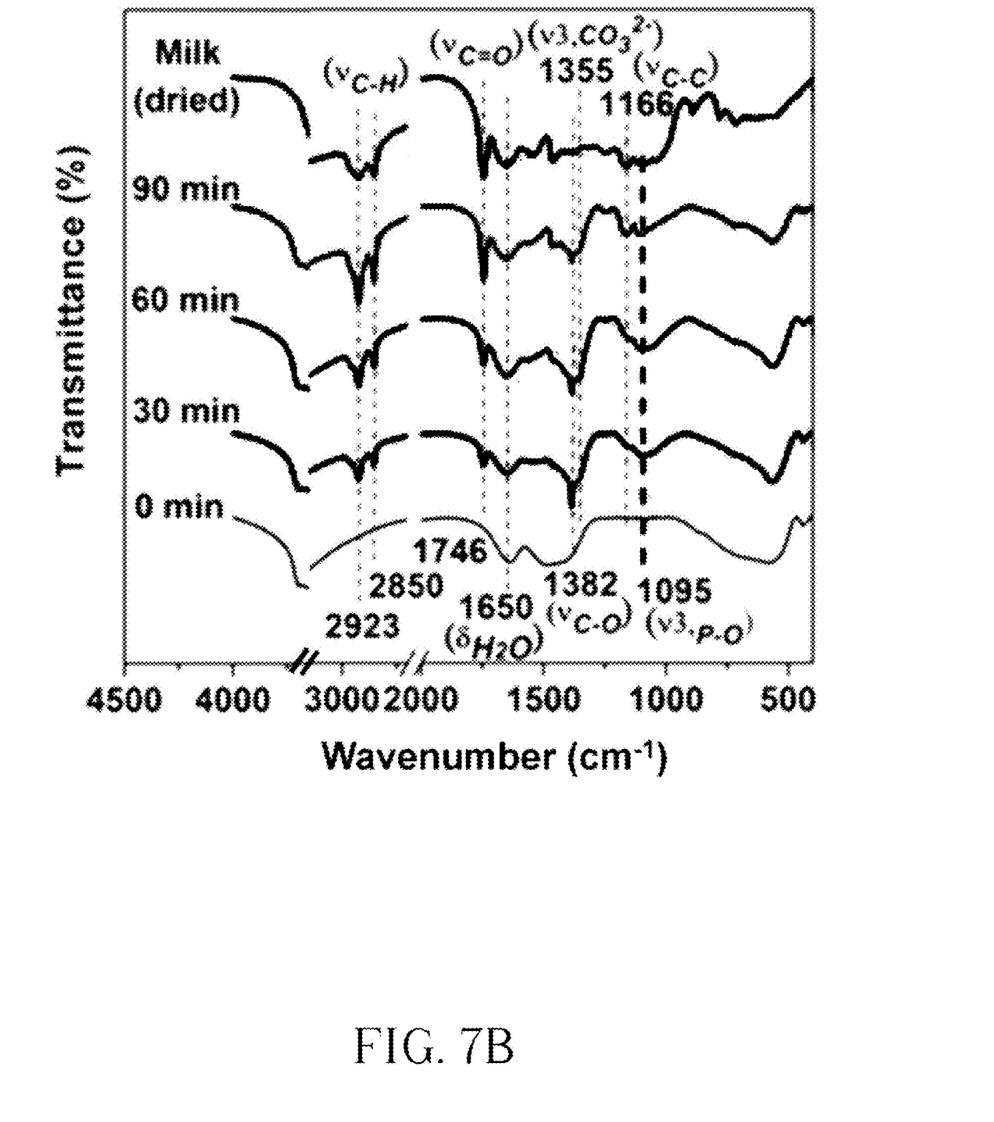
FIG. 7B shows FT-IR spectra of 1 g Mg—Fe—Cl HTln and the HTln spectra after phosphate uptake in 25 ml milk at pH 6.
Figure 8:
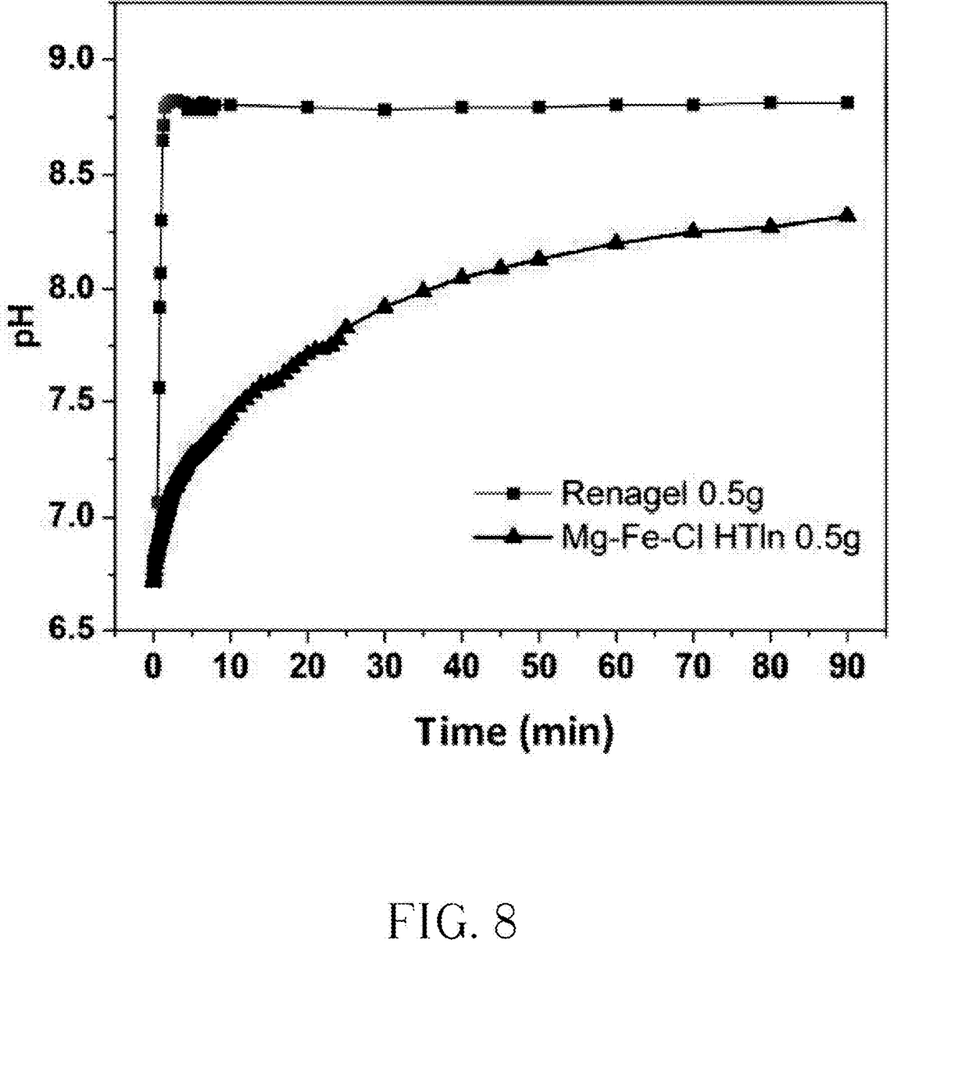
FIG. 8 shows pH variation of 0.5 g Mg—Fe—Cl HTln and 0.5 g Renagel in 25 ml milk as a function of time.

FIG. 6 presents the X-ray diffraction patterns of the Mg—Fe—Cl HTln before and after the phosphorus binding experiments in milk for 90 min. A 1 g mass of Mg—Fe—Cl HTln has the capacity to take up phosphorus in milk, reducing the phosphorus content in milk from 1030 ppm to 359 ppm in 90 min (FIG. 5). As shown in FIG. 6, the X-ray diffraction pattern of the Mg—Fe—Cl HTln after the 90 min experiment was similar to that of the original Mg—Fe—Cl HTln, suggesting that the uptake of phosphorus from milk did not change the layered structure of the HTln. The chemical bonds in the Mg—Fe—Cl HTln after the experiment in milk in different states were identified using FT-IR. FIG. 7A shows the FT-IR spectra of the Mg—Fe—Cl Htln powders with different $Mg^{+2}/Fe^{+3}$ molar ratios for synthesizing the compounds. $Mg(OH)_2$ and $FeCl_3 \cdot 6H_2O$ are the raw materials for the synthetization. In FIG. 7B, $Mg^{+2}/Fe^{+3}$ molar ratios represent the atomic ratio of $Mg^{+2}$ and $Fe^{+3}$ from the raw material used for the synthetization. The FT-IR spectra of the $Mg^{+2}/Fe^{+3}$ molar ratios 2, 4, 8 and 60 from bottom to up were plotted in FIG. 7B. The band that is centered at 426 $cm^{-1}$ is attributed to O-M-O vibration. The broad strong absorption band at 3470 $cm^{-1}$ was attributed to the H-bond stretching vibrations of the OH group ($v_{O-H}$) in the brucite-like layers. The band at 1650 $cm^{-1}$ was attributed to the bending vibration ($\delta_{H_2O}$ of the $H_2O$ molecules in the interlayers. A band at 1355 $cm^{-1}$ corresponds to mode ν of the interlayer carbonate species. FIG. 7B shows FT-IR spectra of 1 g Mg—Fe—Cl HTln (denoted as 0 min) and the HTln spectra after phosphate uptake in 25 ml milk at pH 6 (denoted as 30 min, 60 min and 90 min). The FT-IR spectrum of dried milk powder is also shown for comparison. The band that is centered at 570 $cm^{-1}$ is attributed to M-O-M vibration, which like the M-O-H bending at around 446 $cm^{-1}$, involves translational motion of the oxygen cation in the brucite-like layers. The broad strong absorption band at 3470 $cm^{-1}$ was attributed to the H-bond stretching vibrations of the OH group ($v_{O-H}$) in the brucite-like layers. The band at 1638 $cm^{-1}$ was attributed to the bending vibration ($\delta H_2O$) of the $H_2O$ molecules in the interlayers. A weak band at 1360 $cm^{-1}$ corresponds to mode v3 of the interlayer carbonate species, which was a contaminant from the ambient atmosphere. More importantly, the absorption band at 1095 $cm^{-1}$ which was attributed to the asymmetric vibration of $PO_4$, was clearly identified in the spectra of the HTln samples after the phosphate uptake experiments, indicating that the phosphorus was successfully intercalated into the interlayers of HTln, accompanied by the release of $Cl^-$ (as previously shown in FIG. 3). Mg—Fe—Cl HTln also adsorbed fat, as revealed by the bands at 2923, 2850 and 1746, which are characteristic of fat and associated with vibrations of C—H and C═O bonds. These bands were observed in the spectrum of the dried milk, revealing that the fat was from the milk. FIG. 8 plots the evolution of the pH of 25 ml milk (the milk pH was not maintained) during in the uptake of phosphorus by 0.5 g Renagel and 0.5 g Mg—Fe—Cl HTln, respectively. The pH curve of the milk with the Renagel rose dramatically from 6.7 to 8.8 in 3 min, and was subsequently flat until the end of the experiment. However, the pH curve of the milk with the Mg—Fe—Cl HTln gently increased over time, taking 90 min to reach pH 8.2. This result is attributable to the pH-buffering effect of the HTln. The increase in the alkalinity of the solution with Renagel was much more aggressive than that with Mg—Fe—Cl HTln. Renagel has been reported to have gastrointestinal side effects (nausea, vomiting, abdominal pain, bloating, diarrhea, and constipation) in 38% of patients, perhaps because of the rapid increase in pH and its extensive swelling (FIG. 4) when taken with liquid. Under the pH conditions shown in FIG. 8, according to ICP-AES analysis, 0.5 g Mg—Fe—Cl HTln could uptake ~11% of the phosphorus from the milk in 30 min and ~22% of it at 90 min. Although Renagel removed 30% of the phosphorus from milk in 30 min, but restoration of the phosphorus in the milk was observed beyond 30 min, finally ~26% phosphorus uptake was found at 90 min.

EXPERIMENT 4

Evaluation of In-vitro Cytotoxicity of Mg—Fe—Cl HTln

L929 cells from a mouse fibroblast cell line were used to study the cytotoxicity of Mg—Fe—Cl HTln powder, according to ISO 10993-5 specifications. Mg—Fe—Cl HTln powder was immersed in Dulbecco's modified Eagle's medium (DMEM) (0.02 and 0.2 g/ml) in an incubator under 5% $CO_2$ at 37° C. for different durations (10 min and 12 h). The concentrations (in parts per million (ppm)) of Mg and Fe ions in extracts were analyzed by inductively coupled plasma-mass spectrometry (ICP-MS) with a detection limit of 0.001 ppm for Mg ions and 0.044 ppm for Fe ions. Extracts were then used to treat a cell monolayer for 24 h, and then the cells were examined for morphological changes to assign toxicity scores. Cell viability was evaluated using 3-(4,5-dimethylthiazol-2-yl)-2,5-diphenyl tetrazolium bromide (MTT) assay and the optical density (OD) was measured using a microplate photometer (wavelength 570 nm): higher OD values indicated greater cell viability. The base medium (DMEM) without extract was used as a blank control; DMEM that had been treated with 10% dimethyl sulfoxide was used as a positive control (PC), and a biomedical grade zirconia sheet was used as a negative control (NC). If the cell viability was less than 70% of that of the blank group (medium only), then the extract was considered to be potentially cytotoxic.

Figure 9:
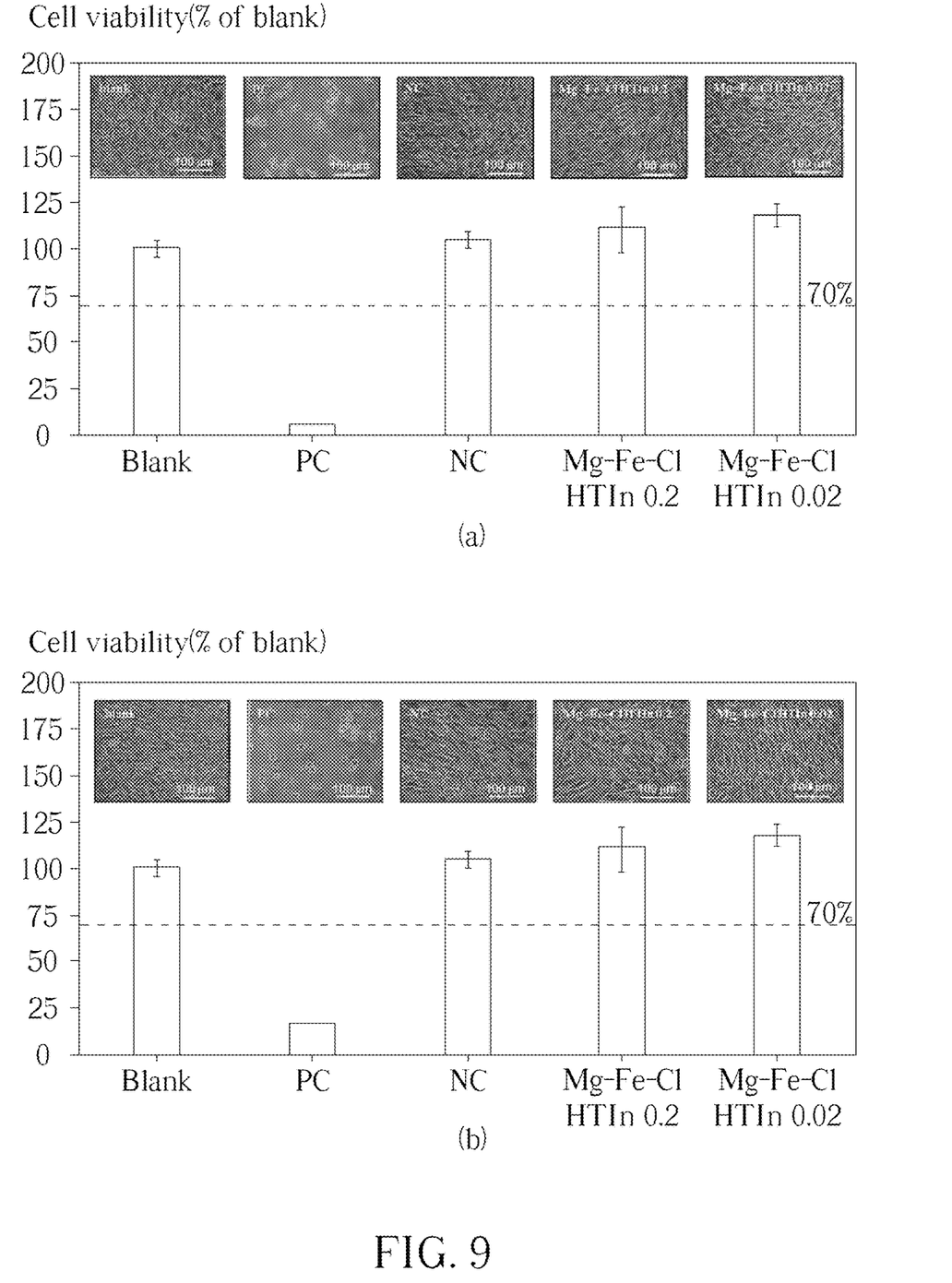
FIG. 9 shows the morphology and viability of L919 cells after culturing medium with Mg—Fe—Cl HTCln.

FIG. 9 presents the morphology and viability of L919 cells after culturing for 24 h in DMEM that contained different doses 0.02 and 0.2 g/ml of extracts of Mg—Fe—Cl HTln powder: FIG. 9(a,b) refer to extracts that were obtained following the immersion of Mg—Fe—Cl HTln powder in the medium for 10 min and 12 h, respectively. As displayed in FIG. 9(a,b), regardless of the extract concentration, L929 cells that were cultured in the extract-containing media were not morphologically different from, and were even slightly more viable than, the cells that were cultured in extract-free media (blank control). These results reveal that the Mg—Fe—Cl HTln powder extracts in this study were potentially non-cytotoxic. In clinical applications, phosphate binders in tablet form (0.8-1.6 g) are taken three times per day with food. Under the assumption that the tablets are taken with 50 ml water, then the concentration of the phosphate binder is 0.016-0.032 g/ml, which is close to the Mg—Fe—Cl HTln powder extract dose 0.02 g/ml that was used herein. A higher Mg—Fe—Cl HTln powder extract dose of 0.2 g/ml was also used to simulate an excessive dose. In this investigation, the phosphate binder was assumed to remain in the human body for less than 6 h (the interval between meals). Mg—Fe—Cl HTln powder extract was obtained after immersion for 12 h, which is the period between dinner and breakfast the following day, whereas Mg—Fe—Cl HTln powder extract was obtained after immersion for 10 min, which corresponds to the rapid absorption of the phosphate binder during a meal. As presented in FIG. 9, no evidence of cytotoxicity of the Mg—Fe—Cl HTln powder was obtained, even when the dose of Mg—Fe—Cl HTln powder or exposure duration exceeded that anticipated for clinical applications. Notably, cell viability in the experimental groups exceeded that in the blank control group. Reducing the concentration of Mg—Fe—Cl HTln powder extract from 0.2 g/ml to 0.02 g/ml would increase cell viability. The human body requires approximately 250-500 mg magnesium daily to maintain physiological processes and the healthy function of cells; the average 70 kg human body contains about 20 g of Mg. Mg ions have been shown to have a marked effect on the phenotype of osteogenic cells both in vivo and in vitro. Fe ions are also essential for metabolic processes, including oxygen transport. Research has established that pure Fe extracts have negligible cytotoxic effects on human endothelial cells. As presented in FIG. 9(b), the fact that Mg—Fe—Cl HTln powder improved cell viability (vs. blank group) is partially attributable to the positive effects of metallic ions (mainly Mg ions) on cell response. Reducing the Mg—Fe—Cl HTln powder extract dose from 0.2 g/ml to 0.02 g/ml further increased cell viability. According to the ICP-MS analysis, the concentrations of Mg and Fe ions in the Mg—Fe—Cl HTln powder extract (dose 0.2 g/ml; immersion time 12 h) were approximately 1800 ppm and 8 ppm, respectively. The Mg—Fe—Cl HTln powder extract at a dose 0.02 g/ml and immersion time of 12 h yielded an Mg ion concentration of around 200 ppm and no detectable Fe ions. This result reveals that approximately <1800 ppm Mg ions have a positive effect on cell viability, whereas a lower concentration (approximately 200 ppm) of Mg ions has an even more positive effect.

EXPERIMENT 5

Figure 10:
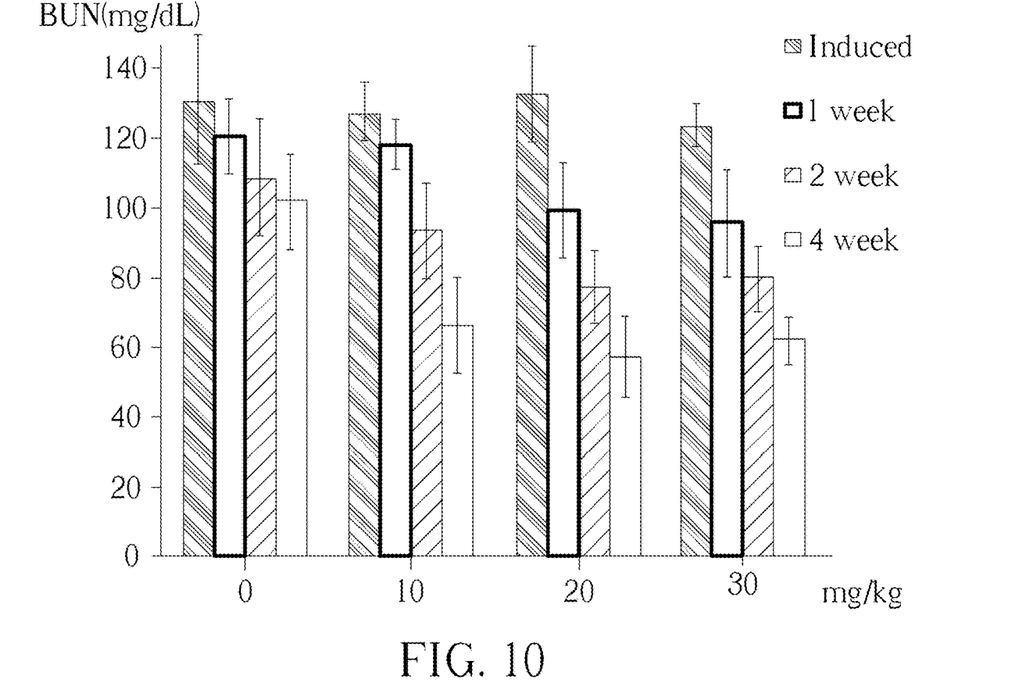
FIG. 10, FIG. 11 and FIG. 12 show bar charts of the serum levels of BUM, creatinine and phosphorus, after administrating Mg—Fe—Cl HCln.
Figure 11:
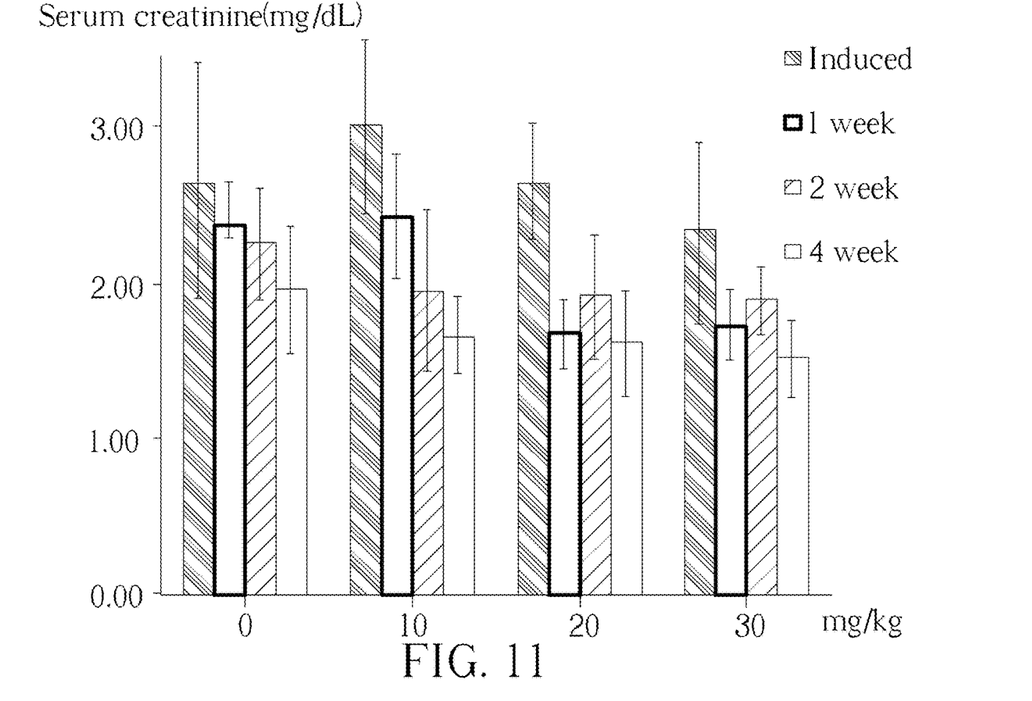
Figure 12:
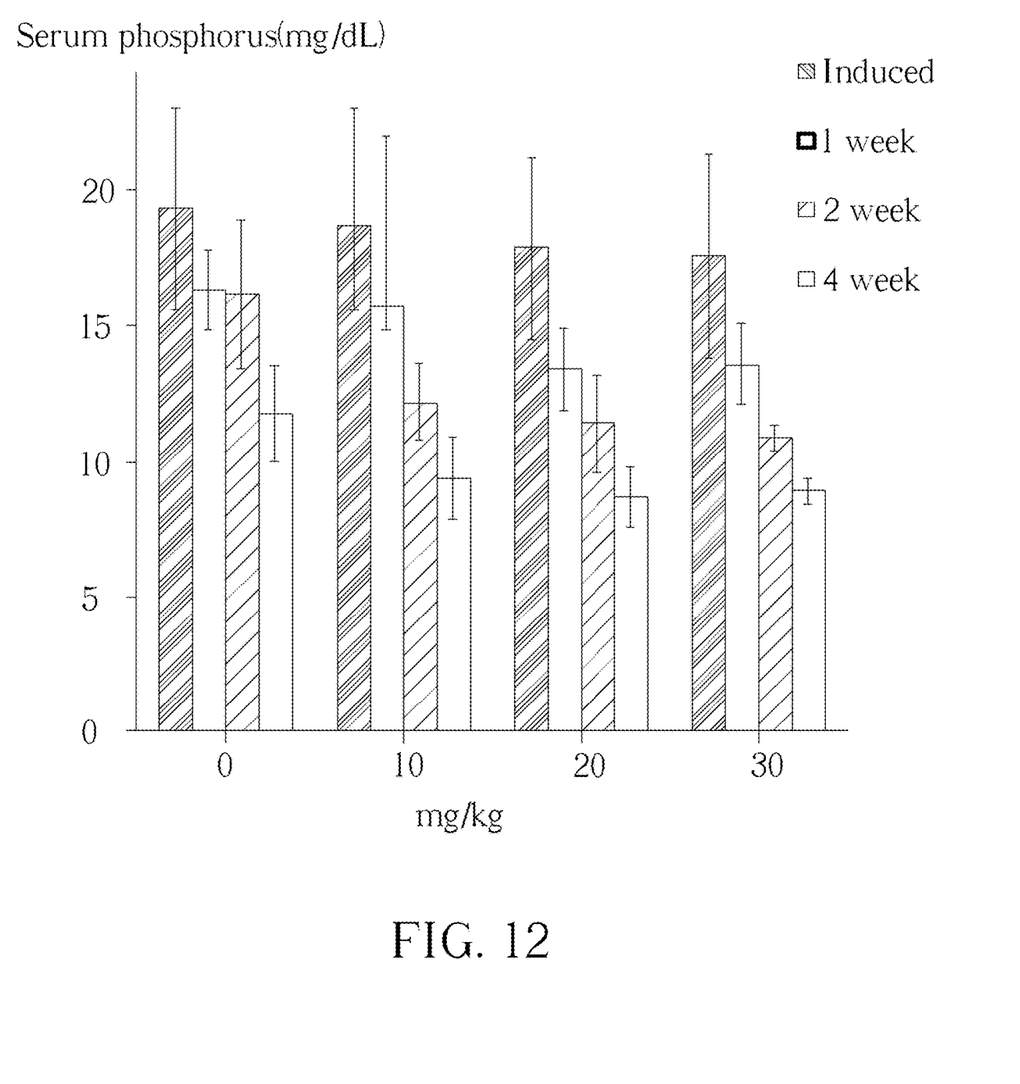

Effect of Dietary Treatment with Mg—Fe—Cl HTln on Serum Levels of BUM, Creatinine, Phosphorus, Calcium, Chlorine, Sodium and Potassium The in vivo effect of Mg—Fe—Cl HCln has been tested by administrating rat with 10 mg/kg, 20 mg/kg, 30 mg/kg Mg—Fe—Cl HCln for 4 weeks. Please refer to FIG. 10, FIG. 11 and FIG. 12, which shows bar charts of the serum levels of BUM, creatinine and phosphorus, after administrating 0 mg/kg, 10 mg/kg, 20 mg/kg, 30 mg/kg Mg—Fe—Cl HCln for 1 week, 2 weeks, 3 weeks and 4 weeks. As shown in FIG. 10, in comparing to control treatment, Mg—Fe—Cl HCln treatment with a dosage of 10 mg/kg, 20 mg/kg and 30 mg/kg can significantly ($P<0.05$) reduce the serum BUM concentration. Similar situation can also be found in FIG. 11 and FIG. 12. Mg—Fe—Cl HCln treatment reduce the serum level of creatinine and phosphorus. It is demonstrated that the Mg—Fe—Cl HCln treatment can effective lowering the BUM level by uptaking the serum phosphorus, suggesting its pharmaceutical function in treating or prophylactically treating patient suffering from hyperphosphatemia. In another experiment, it is shown that the Mg—Fe—Cl treatment does not affect the concentration of serum Ca, serum Cl, serum Na and serum K (data not shown).

In summary, the present invention provides a cationic binder containing Mg—Fe—Cl HCln that can be used as a pharmaceutical composition for treating a patient suffering from or predisposed to hyperphosphatemia. In one embodiment, the Mg—Fe—Cl HCln is shown in formula (I). The phosphorus uptaking capacity of the pharmaceutical composition is greater than 100 ppm/(g/L). The present invention further provides a method for treating a patient suffering from or predisposed to hyperphosphatemia by using said pharmaceutical composition.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A cationic binder, comprising magnesium, iron (III), $H_2O$ and chloride, and an atomic ratio of $Mg^{+2}$ and $Fe^{+3}$ from raw materials used for synthesizing the cationic binder is between 2:1 and 60:1, and an anion uptaking capacity of the cationic binder is greater than 100 ppm/(g/L), wherein a ratio of $H_2O:(Fe^{3+}+Mg^{2+})$ in the cationic binder is between 0.0315 and 0.152.

2. The cationic binder according to claim 1, wherein the raw materials are $Mg(OH)_2$ and $FeCl_3 \cdot 6H_2O$.

3. The cationic binder according to claim 1, wherein a ratio of $Mg^{2+}:Fe^{3+}$ in the cationic binder is between 6:1 and 1.5:1.

4. The cationic binder according to claim 1, wherein the anion uptaking capacity refers to phosphate uptaking capacity.

5. The cationic binder according to claim 1, wherein the cationic binder comprises chloride and carbonate.

6. The cationic binder according to claim 1, wherein the cationic binder comprises formula (I):

$$[Mg_{(1-x)}Fe_x(OH)_{x/n}]^{x+}[Cl]^-_{x(1-2/k)}[CO_3]^{-2}_{x/k} \cdot mH_2O,$$
$$x=0.23\sim0.38 \ n=1.16\sim1.34 \ k=2.37\sim3.28$$
$$m=0.0315\sim0.152 \quad \text{formula (I)}.$$

7. A pharmaceutical composition for treating a patient suffering from or predisposed to hyperphosphatemia, comprising a cationic binder and a pharmaceutically acceptable carrier, wherein the cationic binder comprises magnesium, iron(III) $H_2O$ and chloride, and an atomic ratio of $Mg^{+2}$ and $Fe^{+3}$ from raw materials used for synthesizing the cationic binder is between 2:1 and 60:1, and a anion uptaking capacity of the cationic binder is greater than 100 ppm/(g/L).

8. The pharmaceutical composition according to claim 7, wherein $Mg(OH)_2$ and $FeCl_3 \cdot 6H_2O$ are the raw materials.

9. The pharmaceutical composition according to claim 7, wherein a ratio of $Mg^{2+}:Fe^{3+}$ in the cationic binder is between 4:1 and 2:1.

10. The pharmaceutical composition according to claim 7, wherein the cationic binder has a hydrotalcite-like nanoplatelet (HTln) structure.

11. The pharmaceutical composition according to claim 7, wherein the anion uptaking capacity refers to phosphate uptaking capacity.

12. The pharmaceutical composition according to claim 7, wherein the cationic binder comprises chloride and carbonate.

13. The pharmaceutical composition according to claim 7, wherein the cationic binder comprises formula (I):

$$[Mg_{(1-x)}Fe_x(OH)_{x/n}]^{x+}[Cl]^-_{x(1-2/k)}[CO_3]^{-2}_{x/k} \cdot mH_2O,$$
$$x=0.23\sim0.38 \ n=1.16\sim1.34 \ k=2.37\sim3.28$$
$$m=0.0315\sim0.152 \quad \text{formula (I)}.$$

14. The pharmaceutical composition according to claim 7, wherein the patient comprises human and animal.

15. A method for treating or prophylactically treating a patient suffering from or predisposed to hyperphosphatemia, comprising:
Administering the pharmaceutical composition of claim 1 to a patient.

16. The method according to claim 15, wherein the ratio of $Mg^{2+}:Fe^{3+}$ in the cationic binder is between 6:1 and 1.5:1.

17. The method according to claim 15, wherein the cationic binder has a hydrotalcite-like nanoplatelet (HTln) structure.

18. The method according to claim 15, wherein the anion is divalent phosphate.

19. The method according to claim 15, wherein the cationic binder comprises formula (I):

$$[Mg_{(1-x)}Fe_x(OH)_{x/n}]^{x+}[Cl]^-_{x(1-2/k)}[CO_3]^{-2}_{x/k} \cdot mH_2O,$$
$$x=0.23\sim0.38; \ n=1.16\sim1.34; \ k=2.37\sim3.28;$$
$$m=0.0315\sim0.152.$$

20. The method according to 15, wherein a dosage of the pharmaceutical composition is between 20 mg/kg and 30 mg/kg.

* * * * *